(12) United States Patent
Grand-Clement

(10) Patent No.: US 11,333,901 B2
(45) Date of Patent: May 17, 2022

(54) METHOD FOR DETERMINING THE POSITION OF THE EYE ROTATION CENTER OF THE EYE OF A SUBJECT, AND ASSOCIATED DEVICE

(71) Applicant: Essilor International, Charenton-le-Pont (FR)

(72) Inventor: Didier Grand-Clement, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 182 days.

(21) Appl. No.: 16/624,461

(22) PCT Filed: Jun. 29, 2018

(86) PCT No.: PCT/EP2018/067574
§ 371 (c)(1),
(2) Date: Dec. 19, 2019

(87) PCT Pub. No.: WO2019/002543
PCT Pub. Date: Jan. 3, 2019

(65) Prior Publication Data
US 2020/0218087 A1    Jul. 9, 2020

(30) Foreign Application Priority Data
Jun. 30, 2017 (EP) ..................... 17179209

(51) Int. Cl.
*G02C 7/02*    (2006.01)
*G02C 13/00*    (2006.01)
*A61B 3/00*    (2006.01)

(52) U.S. Cl.
CPC ............ *G02C 7/027* (2013.01); *A61B 3/0025* (2013.01); *G02C 7/028* (2013.01); *G02C 13/005* (2013.01)

(58) Field of Classification Search
CPC ...... G02C 7/027; G02C 13/005; G02C 7/028; A61B 3/0025; A61B 3/0058; A61B 3/1005
See application file for complete search history.

(56) References Cited

U.S. PATENT DOCUMENTS 6,505,936 B1    1/2003 Holladay et al.
2002/0085173 A1    7/2002 Schippert et al.
(Continued)

FOREIGN PATENT DOCUMENTS

AU    2015255562 A1    11/2016
CN    102301270 A    12/2011
(Continued)

OTHER PUBLICATIONS

International Search Report, PCT/EP2018/067574, dated Oct. 23, 2018.
(Continued)

*Primary Examiner* — Jordan M Schwartz
(74) *Attorney, Agent, or Firm* — Nixon & Vanderhye

(57) ABSTRACT

Disclosed is a method for determining the position of the eye rotation center of a subject's eye including: providing a geometric model of an eye, the eye being modeled with one sphere for the sclera and one ellipsoid for the cornea of the eye, the position of the eye rotation center being the distance between a center of the sclera and an apex of the cornea and being determined based on a set of personal parameters including a first geometric dimension of the eye, each personal parameter distinct from the position of the eye rotation center; determining a value of each personal parameter; and determining a first approximate value of eye position rotation center based on the geometric model using the personal parameters. Also disclosed is a method for
(Continued)

calculating a personalized ophthalmic lens for the eye using such center, as well as a device implementing this method.

19 Claims, 2 Drawing Sheets

(56) References Cited

U.S. PATENT DOCUMENTS

| | | | |
|---|---|---|---|
| 2003/0055412 | A1 | 3/2003 | Lieberman et al. |
| 2006/0210122 | A1 | 9/2006 | Cleveland et al. |
| 2009/0040460 | A1 | 2/2009 | Bonnin et al. |
| 2011/0242482 | A1 | 10/2011 | Olsen |
| 2011/0270596 | A1 | 11/2011 | Weeber |
| 2012/0033179 | A1* | 2/2012 | Kratzer .................. A61B 3/111 351/206 |
| 2013/0076884 | A1 | 3/2013 | Choukroun |
| 2013/0083976 | A1 | 4/2013 | Ragland |
| 2014/0232988 | A1 | 8/2014 | Kersting et al. |
| 2015/0029322 | A1* | 1/2015 | Ragland ............. G06K 9/00597 348/78 |
| 2015/0250384 | A1 | 9/2015 | Volkwardt et al. |
| 2015/0293588 | A1* | 10/2015 | Strupczewski .... G06K 9/00597 382/117 |
| 2016/0011437 | A1* | 1/2016 | Nishimura ........... G02C 13/005 351/204 |
| 2016/0302660 | A1 | 10/2016 | Bühren et al. |
| 2017/0071466 | A1* | 3/2017 | Kowal ................ A61B 3/1005 |
| 2019/0333262 | A1* | 10/2019 | Chen .................. G06K 9/00308 |
| 2020/0355945 | A1* | 11/2020 | Abdo ................ H04N 5/23238 |

FOREIGN PATENT DOCUMENTS

| | | |
|---|---|---|
| CN | 103917150 A | 7/2014 |
| CN | 104161496 A | 12/2014 |
| CN | 104520756 A | 4/2015 |
| CN | 105026989 A | 11/2015 |
| CN | 105705982 A | 6/2016 |
| CN | 106461968 A | 2/2017 |
| EP | 2 963 482 | 1/2016 |
| EP | 2 963 483 A1 | 1/2016 |
| FR | 2 762 098 A1 | 10/1998 |
| FR | 3 021 204 A1 | 11/2015 |
| GB | 2 127 959 | 4/1984 |
| WO | 01/24719 A1 | 4/2001 |
| WO | 2006/101943 A2 | 9/2006 |
| WO | 2013/052132 A2 | 4/2013 |
| WO | 2013/178740 A1 | 12/2013 |
| WO | 2015/117904 A1 | 8/2015 |
| WO | 2015/168813 A1 | 11/2015 |
| WO | 2017/054878 A1 | 4/2017 |
| WO | 2018/000020 | 1/2018 |

OTHER PUBLICATIONS

Written Opinion, PCT/EP2018/067574, dated Oct. 23, 2018.
Lefohn et al., "An Ocularist's Approach to Human Iris Synthesis", IEEE Computer Graphics and Applications, vol. 23, issue 6, Nov.-Dec. 2003.
Office Action issued in Chinese Patent Application No. 201880042171.7 dated Jul. 20, 2021.
Office Action issued in Chinese Patent Application No. 201880042171.7 dated Mar. 4, 2022.

* cited by examiner

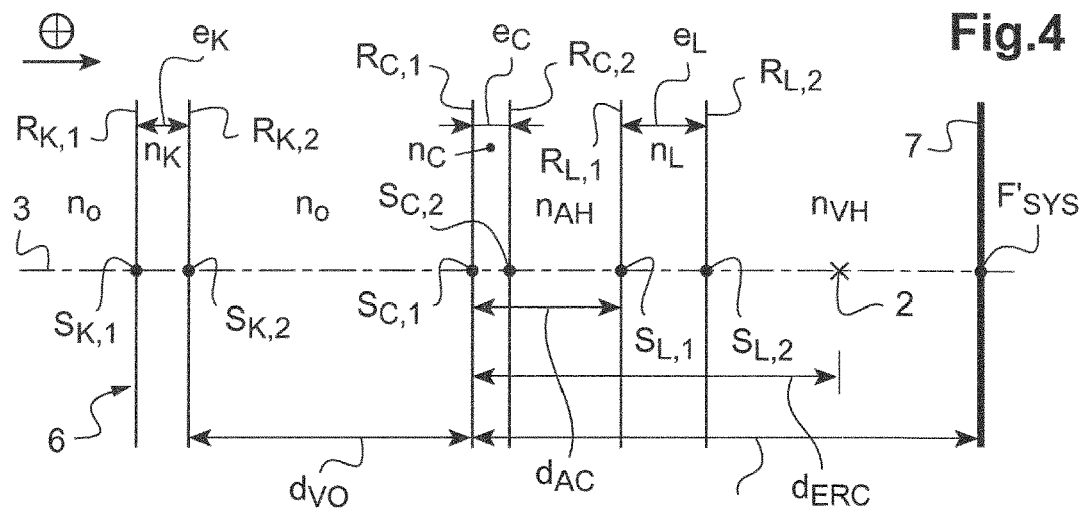
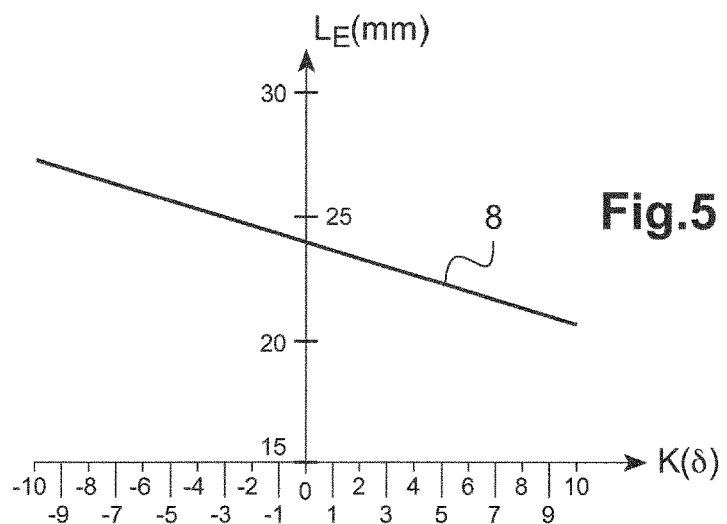
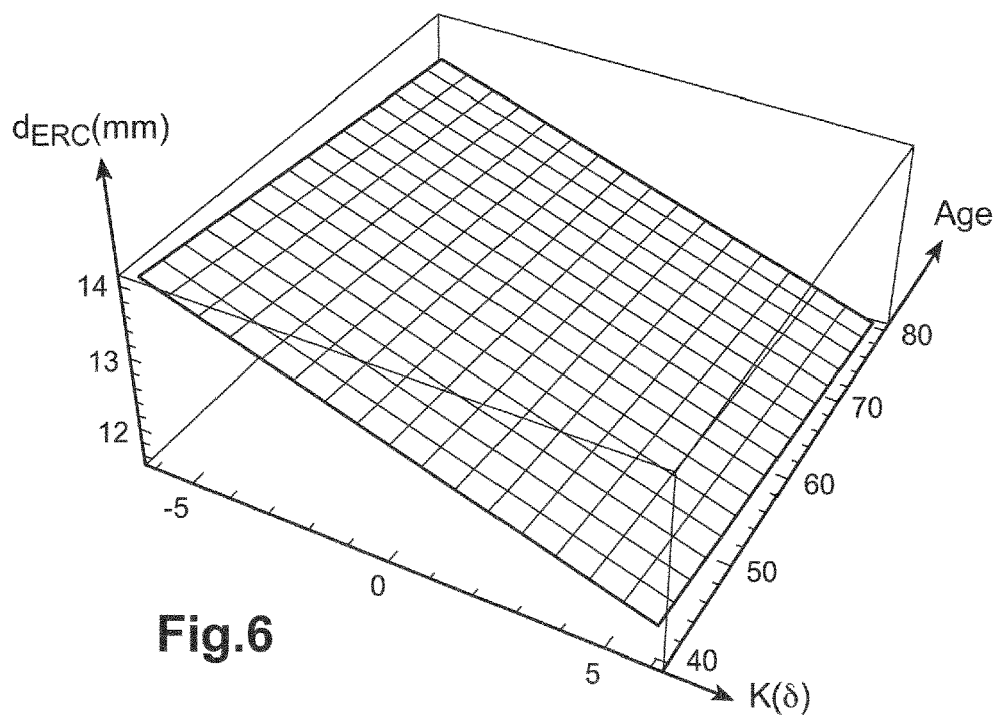

METHOD FOR DETERMINING THE POSITION OF THE EYE ROTATION CENTER OF THE EYE OF A SUBJECT, AND ASSOCIATED DEVICE

TECHNICAL FIELD OF THE INVENTION

The invention relates to the fields of optometry and optical metrology.

More precisely, the invention relates to a device and a method for determining the position of the eye rotation center of the eye of a subject.

The invention relates also to a method for calculating an ophthalmic lens using this method.

BACKGROUND INFORMATION AND PRIOR ART

In order to customize the ophthalmic lens for a specific subject, geometrical, postural and behavioral parameters of the subject and/or of the subject with his/her eyeglasses need to be determined.

Among these parameters, the position of a center of rotation of at least one of the eyes is determined.

Movements of each eye of a subject can generally be considered as being a combination of rotations about a particular point that is referred to as the center of rotation of the eye or "eye rotation center", hereinafter also referred to as ERC.

It is desirable to determine the position of this particular point, for example to perform calculations of a personalized optical design by ray tracing for the corrective lens that is to be fitted properly to a frame chosen by the subject.

In present practice, the position of the ERC may be deduced approximately from the position of the cornea by assuming a mean value for the radius of the eye, typically a value of about 15 millimeters (mm). Such deduction is made for example in document EP 2963482 where the ERC is regarded as being situated 13 mm behind the corneal apex of the eye.

Unfortunately, the radius of the eye varies significantly from one subject to another, such that this approximation leads to significant errors that are highly penalizing for the pertinence of the personalized optical design calculation.

In order to determine the position of the ERC, it is also known a method based on image processing, wherein one captures, by means of an image capture apparatus, at least two facial images of the subject equipped with a reference accessory while the subject looks at this image capture apparatus.

These images are treated in order to determine the ERC. The reference accessory gives information on the relative position of the head of the subject and the image capture device.

Another method is disclosed in Document US 2013/083976, which describes for example a method for determining location and relative motion of the head of a user (starring at a monitor screen) by determining, from digital images of his face, locations of the center points of the two eyeballs of the user.

As shown in details on its FIG. 6, document US 2013/083976 uses a simple model of the eyes based upon Gullstrand's schematic eye, supplemented by generic physiological data. Basically, document US 2013/083976 determines the center point of the apparent iris disc (appearing as an ellipse) and considers that the eyeball center point is simply the point on the optical axis that is one radius distance from the pupil.

However, such method takes time to be carried out and is not particularly well suited to be performed rapidly in the shop of an eye-care practitioner.

Moreover, such method is very precise, whereas a lower level of precision is required, for example to discriminate those patients having an ERC with a position situated outside of the normal range.

SUMMARY OF THE INVENTION

Therefore one object of the invention is to provide an easy-to-implement method to determine quickly an approximate value of the position of the ERC of a subject, in particular without the need of using a reference accessory.

The above object is achieved according to the invention by a method for determining a position of the eye rotation center of an eye of a subject comprising:
  providing a geometric model of an eye, whereby the position of the eye rotation center of this eye is determined based on a set of personal parameters including at least a first geometric dimension of the eye, each personal parameter being distinct from said position of the eye rotation center of the eye;
  determining a value of each personal parameter for the subject; and
  determining a first approximate value of said position of the eye rotation center of the subject in accordance with said geometric model based on the values of the personal parameters.

By "geometric model" of the eye, one understands any physical model adapted to summarize both the optical path of the light through a human eye, and also the movements of this eye.

As the physiological structure of a human eye is very complicated, a complete geometric model of an eye is very hard to elaborate, taking into account all the optical surfaces and physical media involved in the optical path of the light through the eye.

Advantageously, a simple geometric model may be used wherein the geometry of the eye is partially modeled with only two spheres nested one in the other (see Lefohn A. et al., "An ocularist's approach to human iris synthesis", IEEE Computer Graphics and Applications, Vol. 23, Issue 6, November-December 2003). A first part of one sphere can be contemplated as the sclera of the eye: the eye rotation center is positioned at the center of this sphere. A second part of the other sphere can be contemplated as the cornea of the eye.

Another possible geometric model may be used wherein the geometry of the eye is modeled with one sphere for the sclera of the eye and one ellipsoid for the cornea of the eye. In this model, the position of the eye rotation may be determined as a function of:
  the length of the eye;
  the outer diameter of the iris of the eye;
  the eccentricity of the cornea; and
  the depth of the anterior chamber of the eye.

The eccentricity of the cornea may be found by a measurement using an apparatus called an auto kerato-refractometer (also known as "AKR"), for example the VX120 Multi-Diagnostic Unit from the US company Visionix.

With this apparatus, one gets easily the 3D profile of the cornea and one can then find the ellipsoid which models the cornea in the best way.

Other advantageous and non-limiting features of the method according to the invention include:

- said set of personal parameters further comprises at least a second geometric dimension of the eye, said first geometric dimension being measured and said second geometric dimension being assessed;
- the step of assessing said second geometric dimension comprises an evaluation of at least one particular remaining geometric dimension of the eye based on tabulated data comprising several entries, each entry comprising a value of said second geometric dimension in association with at least one corresponding personal characteristic of the subject;
- said corresponding personal characteristic comprises age, gender, and/or ethnicity of the subject;
- the step of assessing said second geometric dimension comprises an evaluation of said second geometric dimension of the eye using an optical model allowing to determine said second geometric dimension based on an optical power of said eye and a need of visual correction for said subject;
- said first geometric dimension of said eye comprises at least one of the following: an outer diameter of an iris of said eye, a front and/or rear shape of a lens of said eye; and/or a distance between a corneal apex and said lens of the eye or a pupil or a plane of the pupil of said eye;
- said geometric model is a model of the sclera and of the cornea of the eye, said sclera being modeled by a first sphere having a first radius and said cornea being modeled by a second sphere having a second radius, said first sphere and said second sphere having a first center and a second center respectively, said first center and said second center defining an optical axis of said eye;
- said method further comprises:
  - acquiring at least one facial image of said eye of the subject; and
  - processing the at least one facial image to derive, from said at least one facial image, an outer diameter of an iris of said eye as said first geometric dimension of the eye;
- said method further comprises:
  - comparing said first approximate value of the position of the eye rotation center with a reference value; and
  - determining a second approximate value of said position of the eye rotation center based on the result of said comparison;
- said method further comprises a calibration step, said at least one facial image including a calibration scale of predetermined length, and the processing step comprises the processing of the image from a dimension of said calibration scale in said facial image;
- when the result of the comparison shows that the difference between the first approximate value and the reference value is larger than a predetermined threshold, the step of determining said second approximate value of the position of said eye rotation center comprises:
  - capturing, thanks to an image-capture device, at least two images of said eye while the subject looks in two different gaze directions;
  - identifying, on each image, the image of the pupil of the eye and determining a geometrical feature of the image of the pupil linked to the shape of this image of the pupil; and
  - determining said second approximate value as a function of said geometrical features of the image of the pupil determined for each image of said plurality of images.
- when the result of the comparison shows that the difference between the first approximate value and the reference value is smaller than a predetermined threshold, the step of determining the second approximate value of the position of said eye rotation center of the eye comprises:
  - feeding said first approximate value to a geometrical database storing values of the position of said eye rotation center of a plurality of subjects; and
  - estimating said second approximate value as being equal to said first approximate value; and
- said predetermined threshold is equal to 0.5 millimeter, preferably equal to 0.1 millimeter.

The invention also relates to a method for calculating a personalized ophthalmic lens for a subject comprising:

- determining a first approximate value of the position of an eye rotation center of an eye of the subject with a method of determination according to the present invention;
- comparing said first approximate value of the position of the eye rotation center with a reference value; and
- when the result of the comparison shows that the difference between the first approximate value and the reference value is smaller than a predetermined threshold, calculating the personalized ophthalmic lens on the basis of the first approximate value of the position of the eye rotation center of the subject.

The invention finally relates to a device for determining a position of the eye rotation center of an eye of a subject.

According to the invention, said device comprises:

- an image-capture apparatus configured to acquire at least one facial image of said eye including at least a portion of said calibration scale;
- image-processing means configured to process said at least one facial image to determine a measured value of an outer diameter of an iris of said eye; and
- calculation means configured to determine a first approximate value of said position of the eye rotation center as a function of said value of an outer diameter of an iris of said eye and of a geometric model of an eye whereby the position of the eye rotation center of the eye is determined based on a set of personal parameters including at least the outer diameter of the iris of the eye, each personal parameter being distinct from said position of the eye rotation center.

The device further comprises a calibration system.

In a first embodiment, the calibration system comprises a calibration scale of predetermined dimension, the image-capture apparatus being further configured to acquire at least one facial image of the eye including at least a portion of said calibration scale.

In a second embodiment, the calibration system comprises an image-capture apparatus that is configured to acquire two distinct facial images of said eye, the image-processing means being configured to determine the measured value of an outer diameter of an iris of said eye on the basis of two distinct facial images.

For instance, in said second embodiment, the image-capture apparatus comprises a first image-capture apparatus and a second image-capture apparatus that are spaced from each other by a predetermined separation distance, each image-capture apparatus being configured to acquire at least one facial image of said eye.

DETAILED DESCRIPTION OF ONE EXAMPLE

The following description, enriched with joint drawings that should be taken as non limitative examples, will help understand the invention and figure out how it can be realized.

On joint drawings:

FIG. 4 is a paraxial representation of the optical model used for the eye of the subject;

FIG. 5 is a curve showing the variation of the length of the eye as a function of the outer diameter of the iris of the subject aged 60;

FIG. 6 is a 3D plot showing the variation of the position of the eye rotation center as a function of age of the subject and need of visual correction for the subject.

Figure 1:
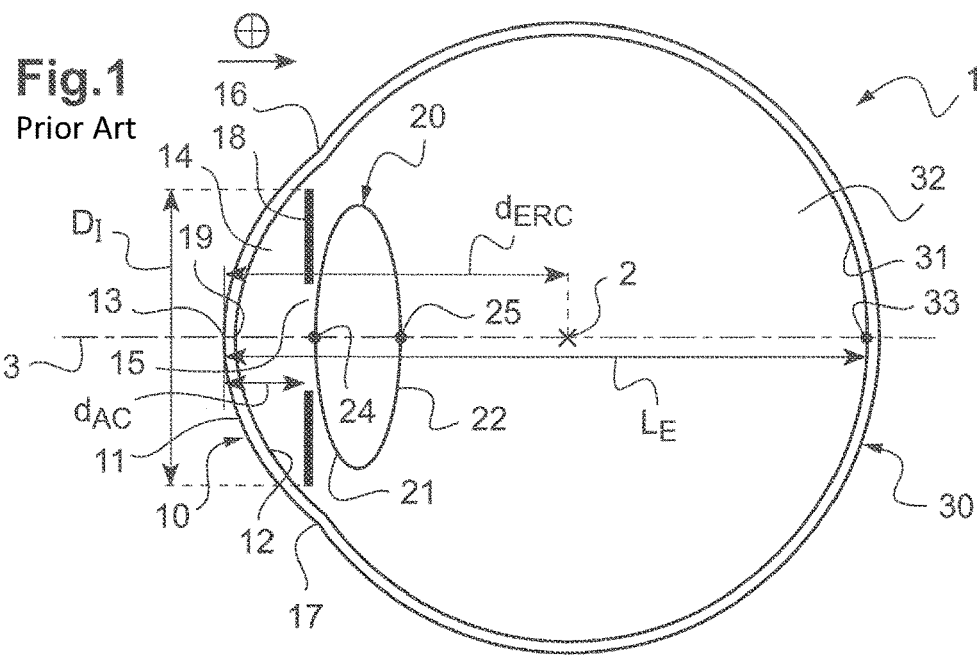
FIG. 1 is a section view of the structure of the eye of a subject.

We represent on FIG. 1 a section view of a simplified physiological structure of a human eye 1 (one the two eyes of a subject, who is not represented on FIG. 1). This structure is basically, with a quite good approximation, a shape of revolution around an optical axis 3, said optical axis 3 passing by the eye rotation center 2 (hereinafter noted ERC) of the eye 1.

It is well-known that the eye 1 comprises mainly a cornea 10, an intra-ocular lens 20 (hereinafter referred to as lens 20) of variable optical power, and a sclera 30.

The cornea 10 is formed by two surfaces 11, 12: a front (anterior) face 11 and a rear (posterior) face 12. Geometrically, those surfaces are in reality very complex, e.g. aspherical, yet in practice, and in the framework of this application, one will assume that the front face 11 and the rear face 12 are substantially spherical surfaces having said optical axis 3 as an axis of revolution (the respective centers of the two spheres are on this optical axis), said optical axis 3 intersecting said surfaces 11, 12 at points 13, 19 (see FIG. 1). In the following, the intersection point 13 will be referred to as the "apex" of the cornea 10. Optically, the front and back faces 11, 12 of the cornea 10 form two optical spherical (concave) diopters of radius $R_{C,1}$ and $R_{C,2}$ which have here positive values with the geometrical convention chosen for FIG. 1 (see arrow at the top of this figure indicating the direction of propagating light).

Right behind the cornea 10 is the anterior chamber 14 of the eye 1 which contains a liquid, the "aqueous humor", which is an optically transparent medium with a refractive index $n_{AH}$ around 1.33. This anterior chamber 14 hence extends from the rear face 12 to the front face 21 of the lens 20, said front face 21 being pressed against the iris 18 of the eye 1 (although in FIG. 1 it is not the case for the sake of clarity), so that the front face 21 of the lens 20 is approximately coplanar with the pupil 15 of the eye 1. The "anterior chamber depth" (hereinafter also referred to as "ACD") is the distance $d_{AC}$ from the rear apex 19 of the cornea 10 to the front apex 24 of the lens 20. This distance $d_{AC}$ is generally comprised between 3 and 4 mm, and decreases with the age of the subject (see below). The iris 18 of the eye 1 clings to the cornea 10 and the sclera 30 at two transitional regions 16, 17 also known as the "corneal limbi" of the eye 1.

Like the cornea 10, the lens 20 is formed by two surfaces 21, 22 of revolution around the optical axis 3: the front face 21 and the rear face 22 of the lens 20. Those lens surfaces 21, 22 are not only of very complex shape—typically aspherical—but also change of shape with accommodation of the eye 1 (increase of the optical power of the eye 1 by modifying the front and/or the shapes of the front and rear surfaces 21, 22). For the sake of simplicity, we will consider in the following description that the eye 1 is here at rest, namely without accommodation and with lowest optical power. In this configuration, the base thickness $t_L$ of the lens 20 between the front apex 24 and the rear apex 25 of the lens 20 is comprised between 3 and 5 mm (the thickness $t_L$ of the lens 20 vary also as a function of accommodation). Optically, the front and back faces 21, 22 of the lens 20 form two optical spherical diopters of radius $R_{L,1}$ (concave, positive) and $R_{L,2}$ (concave, negative) separated by the base thickness $t_L$ of the lens 20.

The rest of the eye 1 is formed by the sclera 30 which takes around 5/6$^{th}$ of circumference of the eye 1, and by the vitreous body 32, which is basically a transparent aqueous liquid contained in the eye 1, filling the space comprised between the rear face 22 of the lens 20 and the retina 31 which partially covers the internal surface of the sclera 30. The optical axis 3 of the eye 1 intersects the retina 31 at the foveal zone 33, also known as the fovea, which is the area of the retina 31 with the highest visual acuity (highest concentration of sensitive photo-receptors) where the images of objects or persons seen by the subject are formed optically.

On the optical axis 3 is the ERC 2 which is aligned with the apex 13 of the cornea 10 and with the fovea 33 of the sclera 30. The distance $L_E$ from the apex 13 to the fovea 33 (see FIG. 2) is referred to as the "length" of the eye 1 and is typically comprised between 20 and 30 mm, more often between 22 mm and 27 mm. The position of the ERC 2 may be determined for example by the raw data of the distance $d_{ERC}$ (see FIG. 1) between the apex 13 of the cornea 10 and the ERC 2.

One can see that the above described structure of the human eye 1 is quite complicated. The position of the ERC 2 may be difficult to determine directly not only because the ERC 2 is internal to the eye 1 but also because its actual position depends on many other parameters, most of them, like the anterior chamber depth $d_{AC}$, lens thickness $t_L$, eye length $L_E$ being difficult to measure directly. By direct measurement, it is meant a simple geometrical measurement, e.g. with a simple graduated ruler.

Therefore, it is one object of the invention to allow determining the position of the ERC 2 indirectly by measuring directly at least one geometric dimension of the eye 1 of the subject.

More precisely, according to the invention, we propose a method for determining the position of the ERC 2 of the eye 1 of the subject, said method comprising the steps of:
- providing a geometric model of an eye, whereby the position of the eye rotation center is determined based on a set of personal parameters including at least a first geometric dimension of the eye, each personal parameter being distinct from said position of the eye rotation center of the eye;
- determining a value of each personal parameter for the subject; and
- determining a first approximate value of said position of the eye rotation center of the subject in accordance with said geometric model based on the values of the personal parameters.

In the preferred embodiment of the invention presented here, the set of personal parameters includes only geometric dimensions of the eye 1.

Figure 2:
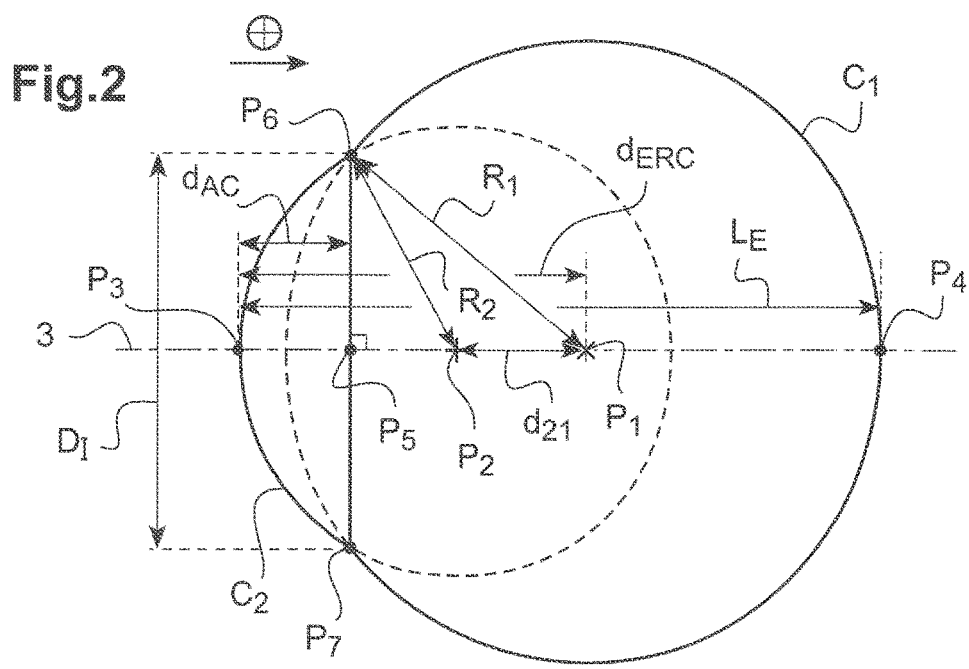
FIG. 2 is a schematic view of one geometric model used for the invention.

We represented on FIG. 2 a possible geometric model of the eye 1 of FIG. 1. This geometric model is built on the assumption that the sclera 30 and the cornea 10 are respectively a part of a first and a second spheres.

More precisely, this geometric model is a model of the sclera 30 and of the cornea 10 of the eye 1, said sclera 30 being modeled (see FIG. 2) by a first sphere (see first circle $C_1$ drawn on FIG. 2) having a first radius $R_1$ and said cornea 10 being modeled by a second sphere (see second circle $C_2$ drawn on FIG. 2) having a second radius $R_2$ smaller than the first radius $R_1$ ($R_2<R_1$), said first sphere and said second sphere having a first center $P_1$ and a second center $P_2$ respectively, said first center $P_1$ and said second center $P_2$ being aligned on a straight line A defining the optical axis 3 of the eye 1.

As obviously shown on FIG. 2, the distance $P_1P_2$ between the two centers $P_1$ and $P_2$ is such that $P_1P_2<(R_1^2-R_2^2)^{1/2}$. Note also that on FIG. 2, these two spheres are represented by two circles $C_1$, $C_2$, whose part drawn with a solid line (- - -) corresponds respectively to the cornea 10 and to the sclera 30. The parts of the circles $C_1$, $C_2$ drawn with a dashed line (- -) on FIG. 2 have no physical reality and have been represented here only of the sake of understanding.

In this simple geometric model, the ERC 2 is positioned at the center $P_1$ of the first circle $C_1$. With this geometric model, we consider that the corneal limbi 16, 17 of the eye 1 in FIG. 1 correspond to the intersection points $P_6$, $P_7$ of the first circle $C_1$ with the second circle $C_2$. The segment $[P_6P_7]$ joining the intersection points $P_6$, $P_7$ may be considered to be in the same plane as the pupil 15 and the iris 18 of the eye 1: it crosses perpendicularly the straight line A (i.e. the optical axis 3) at point $P_5$.

One easily understands that there are only three degrees of liberty in this simple geometric model:
i) the first radius $R_1$ ($R_1=P_1P_4$) of the first circle $C_1$ (modeling sclera 30 and fovea 33);
ii) the second radius $R_2$ ($R_2=P_2P_3$) of the second circle $C_2$ (modeling cornea 10 and apex 13); and
iii) the distance $d_{21}=P_2P_1$ between the center $P_2$ of the second circle $C_2$ (no physical meaning) and the center $P_1$ of the first circle $C_1$, corresponding to the ERC 2 of the eye 1.

Nevertheless, those three geometric dimensions $R_1$, $R_2$, $d_{21}$ are not directly measurable in a simple manner on the subject. Then, we prefer to rebuild the geometric model of the eye 1 of FIG. 1 around the three following geometric dimensions, namely (see FIG. 2):
i') the distance between point $P_3$ (i.e. apex 13) and point $P_4$ (i.e. fovea 33): this distance is the geometric dimension of the eye 1, or eye length $L_E$;
ii') the distance between the point $P_3$ and the point $P_5$ (may be regarded as the front apex 24 of the lens 20): this distance is the geometric dimension of the anterior chamber 14, i.e. the anterior chamber depth $d_{AC}$; and
iii') the distance between the point $P_6$ (upper corneal limbus) and the point $P_7$ (lower corneal limbus): this distance is the geometric dimension of the iris 18 of the eye 1 of the subject, more precisely its outer diameter $D_I$.

Working out the trigonometry in FIG. 2, one can show the following relation (referred to as equation (1)) between the three geometric dimensions $L_E$, $d_{AC}$, $D_I$ and the position of the ERC 2 (geometrically at the center $P_1$ of the first circle $C_1$), e.g. the distance $d_{ERC}$ from the apex 13 of the cornea 10 to the ERC 2:

$$d_{ERC} = \frac{L_E^2 - d_{AC}^2 - \frac{D_I^2}{4}}{2(L_E - d_{AC})}. \tag{1}$$

Hence the problem of determining the position of the ERC 2 is equivalent to the problem of determining the three geometric dimensions $L_E$, $d_{AC}$, $D_I$ of the rebuilt geometrical model.

Among the selected geometric dimensions $L_E$, $d_{AC}$, $D_I$, the outer diameter $D_I$ of the iris 18 may be easily measured geometrically. One thus may choose the outer diameter $D_I$ of the iris 18 as the first geometric dimension of the eye 1 of the subject to be included in the geometric model.

In a preferred embodiment, the step of measuring a first value of the outer diameter $D_I$ of the iris 18 comprises:
a first sub-step of image acquisition wherein one acquires a facial image 4 (see FIG. 3) of said eye 1 of the subject, said facial image 4 including a calibration scale 5 of predetermined length (1 mm in the case of FIG. 3, meaning that the real length of the scale 5 is 1 mm, whatever the actual length in the facial image 4); and
a second sub-step of image processing wherein one process the facial image 4 (which is generally a digital image) to derive, from said facial image 4 and from the dimension of said calibration scale 5 (i.e. its actual length) in the facial image 4, the outer diameter $D_I$ of the iris 18.

Figure 3:
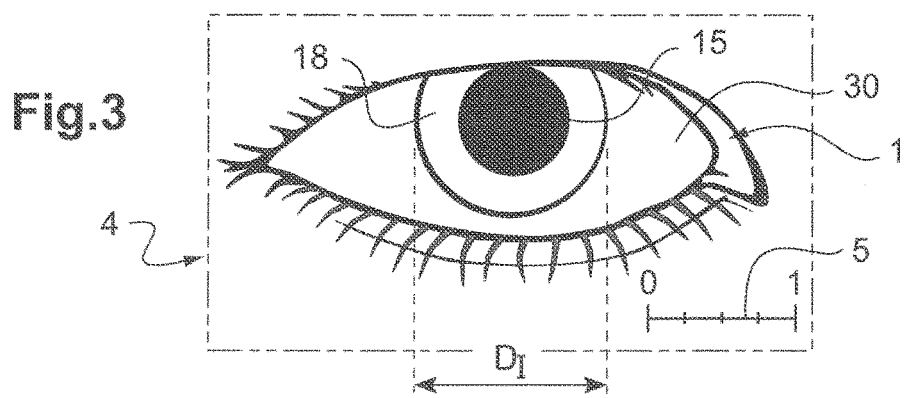
FIG. 3 is a facial image of the eye of a subject acquired by a device according to the invention.

To implement this method, the invention also provides a device for determining the position $d_{ERC}$ of the eye rotation center 2 of the eye 1 of the subject, said device comprising:
a calibration scale of predetermined length like the one drawn in FIG. 3;
an image-capture apparatus, such as a digital camera for example, configured to acquire at least one facial image of the eye which includes at least a portion of said calibration scale;
image-processing means configured to process the facial image to determine a measured value of an outer diameter of an iris of said eye; and
calculation means configured to determine an approximate value of said position of the eye rotation center as a function of said value of the outer diameter $D_I$ of the iris 18, said calculation means implementing a method for determining said position of the eye rotation center as described above.

The present device is obviously not limited to a calibration scale, and we can imagine any other calibration system that would be configured so that the calculation means can determine an approximate value of the position of the eye rotation center on the basis of a facial image of the eye.

Hence, the calculation means comprise a geometric model of the eye of the subject such as, for example, the one described above (2-spheres model).

The image-processing means and calculation means may be a computer receiving the facial image from the image-capture apparatus.

In another embodiment, the device for determining a position of the eye rotation center of an eye of a subject comprises:
a first image-capture apparatus and a second image-capture apparatus spaced from each other by a predetermined separation distance, each image-capture apparatus being configured to acquire at least one facial image of said eye;

image-processing means configured to process the two facial images acquired by the two image-capture apparatus to determine a measured value of an outer diameter of an iris of said eye; and calculation means configured to determine an approximate value of said position of the eye rotation center as a function of said value of an outer diameter of an iris of said eye.

Such device is described in the document WO 2015/101737 in the name of the applicant.

In a variant of the method, the step of measuring a first value of the outer diameter $D_I$ of the iris 18 may comprise:

a) determining the real inter-pupil distance between the two eyes of the subject (this can be done easily at the optician's shop);

b) acquiring a facial image of the whole face of the subject, said image including the images of the two eyes of the subject;

c) evaluating the actual dimension of inter-pupil distance between the two images of the eyes in the facial image of the whole face; and d) deriving a value for the outer diameter $D_I$ of the eye from the inter-pupil distance.

Then, in the method according to the invention, one assesses the remaining values of the remaining geometric dimensions of the geometric model, that is the eye length $L_E$; and the anterior chamber depth $d_{AC}$ (the distance between point $P_3$ and $P_5$ in FIG. 2).

In the preferred embodiment of the invention described here, one evaluates the anterior chamber depth $d_{AC}$ based on tabulated data gathered among a large number of subjects. The anterior chamber depth can be measured using an apparatus called an auto kerato-refractometer (also known as "AKR"), for example the VX120 Multi-Diagnostic Unit from the US company Visionix.

Advantageously, one may sort out the measured values of the anterior chamber depth based on age, gender, and/or ethnicity of the subject, so that one can interpolate and/or extrapolate a mathematical rule to assess the value of the anterior chamber depth $d_{AC}$ as a function of these personal parameters of the subject.

At this stage, one got:

1) a measured first value for the outer diameter $D_I$ of the iris 18 of the eye 1 of the subject; and 2) an assessed value of the anterior chamber depth $d_{AC}$ based on tabulated data depending on personal parameters of the subject.

According to Eq. 1 above, a value of the eye length $L_E$ shall be now assessed in order to determine the position (here the distance $d_{ERC}$, see FIG. 2) of the ERC 2 of the eye 1 of the subject.

Like the anterior chamber depth $d_{AC}$, one could estimate the eye length $L_E$ based on other tabulated data, eventually depending on personal parameters of the subject.

Yet, in the preferred embodiment described here, one evaluates the eye length $L_E$ using an optical model which allows determining said eye length $L_E$ based on the objective optical power $P_E$ of said eye 1 and a subjective need K of visual correction for said subject (both optical power $P_E$ and need K of visual correction are expressed in diopters).

Again, the optical power $P_E$ of said eye 1 may be either measured (using for example the same apparatus VX110) directly or evaluated directly using tabulated data, eventually depending on personal parameters of the subject.

Here, one prefers using a complete optical model of the eye 1, wherein the eye length $L_E$, which is the geometric distance between the apex 13 of the cornea 10 and the fovea 33 of the sclera 30, can be calculated, in the paraxial approximation, as a function of geometric and optical parameters of the eye 1.

We have represented in FIG. 4 a schematic optical drawing, in the paraxial approximation, of the eye 1 of the subject, here with a corrective ophthalmic lens 6 corresponding to the need K of visual correction for the subject.

The different references in this FIG. 4 are the following:

$n_o$: refractive index of ambient air;

$n_K$: refractive index of the corrective ophthalmic lens 6

$S_K$ and $R_{K,1}$: apex and radius of curvature of the first diopter (air/lens) of the ophthalmic lens 6;

$S_{K,2}$ and $R_{K,2}$: apex and radius of curvature of the second diopter (lens/air) of the ophthalmic lens 6;

$d_{VO}$: distance between the ophthalmic lens 6 and the eye 1;

$e_C$, $n_C$: thickness and refractive index and of the cornea 10;

$S_{C,1}$ and $R_{C,1}$: apex and radius of curvature of the first diopter (air/cornea) of the cornea 10;

$S_{C,2}$ and $R_{C,2}$: apex and radius of curvature of the second diopter (cornea/air) of the cornea 10;

$n_{AH}$: refractive index of the aqueous humor;

$d_{AC}$: the anterior chamber depth;

$e_L$, $n_L$: thickness and refractive index and of the intraocular lens 20;

$S_{L,1}$ and $R_{L,1}$: apex and radius of curvature of the first diopter (aqueous humor/lens) of the cornea 10;

$S_{L,2}$ and $R_{L,2}$: apex and radius of curvature of the second diopter (lens/vitreous humor) of the cornea 10;

$n_{VH}$: refractive index of the vitreous humor;

$F'_{sys}$: image focal length of the whole optical system formed by the ophthalmic lens. With its refractive correction and at rest, the eye 1 is such that $F'_{sys}$ is positioned on the retina plane 7 (paraxial approximation), more precisely at the fovea 33.

From FIG. 4, it is clear that the eye length $L_E$ is the distance from the apex $S_{C,1}$ (apex 13 of FIG. 1) of the cornea 10 to the image focal length $F'_{SYS}$ (fovea 33 of FIG. 1):

$$L_E = |\overline{S_{C,1}F'_{SYS}}| = \overline{S_{C,1}F'_{SYS}} > 0$$

The cornea 10, with its two apex $S_{C,1}$ and $S_{C,2}$, may be, in the optical paraxial approximation, modeled by a centered system having an optical power $P_C$ given by the well-known Gullstrand's formula:

$$P_C = P_{C,1} + P_{C,2} - \frac{e_C}{n_C} \times P_{C,1} \times P_{C,2} \qquad (2)$$

$$P_{C,1} = \frac{n_C - n_0}{R_{C,1}} \qquad (3)$$

$$P_{C,2} = \frac{n_{AH} - n_C}{R_{C,2}} \qquad (4)$$

and principal points $H_C$ (object) and $H'_C$ (image) given by $$\overline{S_{C,1}H_C} = n_0 \times \frac{e_C}{n_C} \times \frac{P_{C,2}}{P_C} \qquad (5)$$

$$\overline{S_{C,1}H'_C} = e_C \times \left[1 - \frac{n_{AH}}{n_C} \times \frac{P_{C,1}}{P_C}\right]. \qquad (6)$$

In the same way, the lens 20, with its two apex $S_{L,1}$ and $S_{L,2}$, may be, in the paraxial approximation, modeled by a centered system having an optical power $P_L$ given by the Gullstrand's formula:

$$P_L = P_{L,1} + P_{L,2} - \frac{e_L}{n_L} \times P_{L,1} \times P_{L,2} \quad (7)$$

$$P_{L,1} = \frac{n_L - n_{AH}}{R_{L,1}} \quad (8)$$

$$P_{L,2} = \frac{n_{VH} - n_L}{R_{L,2}} \quad (9)$$

and where principal points $H_L$ (object) and $H'_L$ (image) are such that:

$$\overline{S_{C,1}H_L} = d_{AC} + n_{AH} \times \frac{e_L}{n_L} \times \frac{P_{L,2}}{P_L} \quad (10)$$

$$\overline{S_{C,1}H'_L} = d_{AC} + e_L \times \left[1 - \frac{n_{AH}}{n_L} \times \frac{P_{L,1}}{P_L}\right]. \quad (11)$$

Using Equations (6) and (10), one gets:

$$\overline{H'_C H_L} = d_{CL} = \quad (12)$$

$$\overline{H'_C H_{C,1}} + \overline{S_{C,1}H_L} = d_{AC} - e_C + n_{AH} \times \left[\frac{e_C}{n_C} \times \frac{P_{C,1}}{P_C} + \frac{e_L}{n_L} \times \frac{P_{L,2}}{P_L}\right]$$

and the objective optical power $P_E$ of the eye 1 by the following equation:

$$P_E = P_C + P_L - \frac{d_{CL}}{n_{AH}} \times P_C \times P_L. \quad (13)$$

Again, using Gullstrand's formulas, one derives the principal points $H_E$ (object) and $H'_E$ (image) of the eye 1 (made up by association of cornea 10 and lens 20) as:

$$\overline{H_C H_E} = n_0 \times \frac{d_{CL}}{n_{AH}} \times \frac{P_L}{P_E} \quad (14)$$

$$\overline{H'_L H'_E} = -n_{VH} \times \frac{d_{CL}}{n_{AH}} \times \frac{P_C}{P_E}. \quad (15)$$

Then, it comes:

$$\overline{S_{C,1}H_E} = \overline{S_{C,1}H_C} + \overline{H_C H_E} \quad (16)$$

$$\overline{S_{C,1}H'_E} = \overline{S_{C,1}H'_L} + \overline{H'_L H'_E}. \quad (17)$$

By definition, the object focal length $f_E$ and the image focal length $f'_E$ of the eye are given by:

$$\overline{H_E F_E} = f_E = \frac{-n_0}{P_E} \quad (18)$$

$$\overline{H'_E F'_E} = f'_E = \frac{n_{VH}}{P_E} \quad (19)$$

so that:

$$\overline{S_{C,1}F_E} = \overline{S_{C,1}H_E} + f_E \quad (20)$$

$$\overline{S_{C,1}F'_E} = \overline{S_{C,1}H'_E} + f'_E. \quad (21)$$

Now, one considers the whole optical system formed by:
the corrective ophthalmic lens 6 of optical power $P_K$ ($P_K=K$) eventually worn by the subject ($P_K=0$ if the subject does not need any visual correction); and
the eye 1 of the subject,
and one calculates the total optical power $P_{SYS}$ of this system as:

$$P_{SYS} = P_K + P_E - \frac{d_{KE}}{n_0} \times P_K \times P_E \quad (22)$$

$$d_{KE} = \overline{H'_K H_E} = \overline{H'_L S_{C,1}} + \overline{S_{C,1} H_E} \quad (23)$$

Moreover, again using Gullstrand's formula, one got:

$$\overline{H'_E H'_{SYS}} = -n_{VH} \times \frac{d_{KE}}{n_0} \times \frac{P_K}{P_{SYS}} \quad (24)$$

$$\overline{H'_{SYS} F'_{SYS}} = f'_{SYS} = \frac{n_{VH}}{P_{SYS}} \quad (25)$$

And, at the end, one obtains the final equation giving the eye length $L_E$ of the subject based on all the optical parameters of FIG. 4:

$$\overline{S_{C,1}F'_{SYS}} = L_E = \overline{S_{C,1}H'_E} + \overline{H'_E H'_{SYS}} + f'_{SYS}. \quad (26)$$

From those calculations, one can make the following remarks:

A) the eye length $L_E$ depends on (see FIG. 4):
the refractive index of ambient air $n_0 \approx 1.00$;
all the geometric or optical parameters of the eye 1: $e_C$, $n_C$, $R_{C,1}$, $R_{C,2}$, $n_{AH}$, $e_L$, $n_L$, $R_{L,1}$, $R_{L,2}$, $n_{VH}$,
the anterior chamber depth $d_{AC}$;
the equivalent lens-eye distance $\overline{H'_E S_{C,1}} > 0$ (depending on the geometric or optical properties of the lens, namely $e_K$, $n_K$, $R_{K,1}$, $R_{K,2}$ and the actual lens-eye distance $d_{VO}$); and
the need K of visual correction ($P_K=K$) of the subject.

B) the above-mentioned variables $n_0$, $e_C$, $n_C$, $R_{C,1}$, $R_{C,2}$, $n_{AH}$, $e_L$, $n_L$, $R_{L,1}$, $R_{L,2}$, $n_{VH}$, $d_{AC}$ may be either measured or estimated using tabulated data which may eventually depend on personal data of the subject as the age, the gender and/or the ethnicity;

C) if the subject does not need any visual correction, that is K=0, then $P_K=0$ and $F'_{SYS}=F'_E$ ($P_{SYS}=P_E$), so that $L_E=\overline{S_{C,1}H'_E} + f'_E$.

FIG. 5 shows an example of result for the calculation of the eye length $L_E$ as a function of the outer diameter $D_I$ of the iris 18 of the eye 1 of the subject. This result has been obtained using the data tabulated for the above-mentioned variables from Tan, Bo, "*Optical Modeling of Schematic Eyes and the Ophthalmic Applications*"—PhD dissertation, University of Tennessee, 2009—http://trace.tennessee.edu/utk qraddiss/63.

The tabulation has been made as a function of both AGE of the subject and need K of visual correction for the subject. Below are the expressions of the different variables used for the calculation of FIG. 5:

$n_C=1.3771$
$e_C=0.55$
$R_{C,1}=7.75+0.016*K$
$R_{C,2}6.5+0.013*K$
$n_{AH}=1.3374$ $d_{AC}$=3.909−0.0105*AGE
$n_L$=1.42
$e_L$=3.46+0.013*AGE
$R_{L,1}$=12.283−0.0438*AGE
$R_{L,2}$=−6.0
$n_{VH}$=1.336

For FIG. 5, one assumes that $\overline{H'_K S_{C,1}}$=13.75 mm, which is a common value used with standard auto-refractometer. One then traced the curve 8 of the length of the eye $L_E$ for a subject being 60 years old (AGE=60).

On this figure, one can see that the eye length $L_E$ is comprised between around 20 mm and 28 mm.

Moreover, one can see that the curve 8 is a quasi straight line, showing that the eye length $L_E$ varies linearly with the need K in visual correction.

Finally, from this FIG. 5, one recovers the fact that, on one hand, a nearsighted eye (needing a negative power of correction, i.e. a divergent ophthalmic lens) is longer than the "normal" eye (needing no power of correction, K=0), and, on the other end, a farsighted eye (needing a positive power of correction, i.e. a convergent ophthalmic lens) is shorter than the "normal" eye.

FIG. 6 shows a 3D plot of the position dERC of the ERC 2 of the eye 1 of the subject as a function of age and need K (in diopters) of visual correction.

On this figure, one rediscovers that a myopic eye, needing negative correction (K<0, divergent ophthalmic lens), is longer than a "normal" eye without such need (K=0). The same is true for a hypermetropic eye (need K>0; convergent ophthalmic lens) which is too short. For an age of 40 years, one sees that:

the position $d_{ERC}$ of the ERC 2 of the eye 1 is around 13.5 mm for a "normal" eye (K=0); and the difference in the position $d_{ERC}$ is as high as 2 mm (for an eye length of about 25 mm) for the two extreme cases (K=−6 δ and K=+6 δ).

Preferably, after having determined a first approximate value of the position $d_{ERC}$ of the ERC 2 performing the different steps above, one then compares said first approximate value with a reference value $d_{ERC,ref}$, e.g. found in a geometrical database which stores an huge amount of measured values of the position $d_{ERC}$ as function of age, need in visual correction, gender, and/or ethnicity, etc. . . . ; and one determines a second approximate value of said position of the eye rotation center based on the result of said comparison.

In practice, when the result of the comparison shows that the difference $\Delta d_{ERC}$=|$d_{ERC}$−$d_{ERC,ref}$| between the approximate value $d_{ERC}$ and the reference value $d_{ERC,ref}$ is smaller than a predetermined threshold equal to 0.5 millimeter, preferably equal to 0.1 mm, the step of determining the second approximate value of the position of said eye comprises:

feeding said first approximate value $d_{ERC}$ to the geometrical database which stores values of the position of said eye rotation center of a plurality of subjects; and estimating said second approximate value as being equal to the first approximate value $d_{ERC}$.

On the contrary, when the result of the comparison shows that the difference between the approximate value $d_{ERC}$ and the reference value $d_{ERC,ref}$ is larger than the predetermined threshold, determining the second approximate value of the position of said eye rotation center comprises:

capturing, thanks to an image-capture device, at least two images of said eye while the individual looks in two different gaze directions;

identifying, on each image, the image of the pupil of the eye and determining a geometrical feature of the image of the pupil linked to the shape of this image of the pupil; and determining said second approximate value as a function of said geometrical features of the image of the pupil determined for each image of said plurality of images.

A description of this step of determining the second approximate value of the position of said eye rotation center may be found in the not-published document EP 16 306 302.7 in name of the applicant.

The invention claimed is:

1. A method for determining a position ($d_{ERC}$) of the eye rotation center of an eye of a subject comprising:

providing a geometric model of an eye, whereby the eye is modeled with one sphere (C1) for the sclera of the eye and one substantially spherical surface (C2) for the cornea of the eye, the position of the eye rotation center of this eye corresponding to a center (P1) of the sclera and being determined by the distance ($d_{ERC}$) between said center and an apex of the cornea and being determined based on a set of personal parameters ($L_E$, $d_{AC}$, $D_I$, $A_{GE}$, K) including at least a first geometric dimension ($D_I$) of the eye, each personal parameter ($L_E$, $d_{AC}$, $D_I$, $A_{GE}$, K) being distinct from said position of the eye rotation center of the eye;

determining a value of each personal parameter ($L_E$, $d_{AC}$, $D_I$, $A_{GE}$, K) for the subject; and determining a first value of said eye rotation center (P1) by mathematically calculating said distance ($d_{ERC}$) of the subject in accordance with said geometric model based on the values of the personal parameters ($L_E$, $d_{AC}$, $D_I$, $A_{GE}$, K), wherein said set of personal parameters ($L_E$, $d_{AC}$, $D_I$, $A_{GE}$, K) further comprises at least a second geometric dimension ($L_E$) of the eye, said first geometric dimension ($D_I$) being measured and said second geometric dimension being assessed by assigning values, rather than measuring values, based on personal characteristics of the subject.

2. The method according to claim 1, wherein the step of assessing said second geometric dimension comprises an evaluation of at least one additional geometric dimension of the eye based on tabulated data comprising several entries, each entry comprising a value of said second geometric dimension in association with at least one corresponding personal characteristic of the subject.

3. The method according to claim 2, wherein said corresponding personal characteristic comprises one of age ($A_{GE}$), gender, and/or ethnicity of the subject.

4. The method according to claim 1, wherein the step of assessing said second geometric dimension ($L_E$) comprises an evaluation of said second geometric dimension ($L_E$) of the eye using an optical model allowing to determine said second geometric dimension ($L_E$) based on an optical power ($P_E$) of said eye and a need (K) of visual correction for said subject.

5. The method according to claim 1, wherein said first geometric dimension ($D_I$) of said eye comprises at least one of the following:

an outer diameter ($D_I$) of an iris of said eye;
a front and/or rear shape of a lens of said eye; and/or
a distance ($d_{AC}$) between a corneal apex and said lens of the eye or a pupil or a plane of the pupil of said eye.

6. The method according to claim 1, wherein said geometric model is a model of the sclera and of the cornea of the eye, said sclera being modeled by a first sphere ($C_1$)

having a first radius ($R_1$) and said cornea being modeled by a second sphere ($C_2$) having a second radius ($R_2$), said first sphere ($C_1$) and said second sphere ($C_2$) having a first center ($P_1$) and a second center ($P_2$) respectively, said first center ($P_1$) and said second center ($P_2$) defining an optical axis of said eye.

7. The method according to claim 1, further comprising:
acquiring at least one facial image of said eye of the subject; and
processing the at least one facial image to derive, from said at least one facial image, an outer diameter ($D_I$) of an iris of said eye as said first geometric dimension of the eye.

8. The method according to claim 1, further comprising:
comparing said first value of the position ($d_{ERC}$) of the eye rotation center with a reference value ($d_{ERC,ref}$); and
determining a second value of said position ($d_{ERC}$) of the eye rotation center based on the result of said comparison.

9. The method according to claim 8, wherein, when the result of the comparison shows that the difference ($\Delta d_{ERC}$) between the first value and the reference value is larger than a predetermined threshold, determining the second value of the position ($d_{ERC}$) of said eye rotation center comprises:
capturing, by an image-capture device, at least two images of said eye (1) while the subject looks in two different gaze directions;
identifying, on each image, the image of the pupil of the eye and determining a geometrical feature of the image of the pupil linked to the shape of this image of the pupil; and
determining said second value as a function of said geometrical features of the image of the pupil determined for each image of said plurality of images.

10. The method according to claim 8, wherein, when the result of the comparison shows that the difference ($\Delta d_{ERC}$) between the first value and the reference value is smaller than a predetermined threshold, the step of determining the second value of the position ($d_{ERC}$) of said eye rotation center of the eye comprises:
feeding said first value to a geometrical database storing values of the position of said eye rotation center of a plurality of subjects; and
estimating said second value as being equal to the first value.

11. A method for calculating a personalized ophthalmic lens for a subject comprising:
determining a first value of the position ($d_{ERC}$) of the eye rotation center of an eye of the subject with a method of determination according to claim 1;
comparing said first value of the position ($d_{ERC}$) of the eye rotation center with a reference value ($d_{ERC,ref}$); and
when the result of the comparison shows that the difference between the first value and the reference value is smaller than a predetermined threshold, calculating the personalized ophthalmic lens on the basis of the first value of the position ($d_{ERC}$) of the eye rotation center of the subject.

12. The method according to claim 9, wherein said predetermined threshold is equal to 0.5 millimeter.

13. A method for determining a position of the eye rotation center of an eye of a subject comprising:
an image-capture apparatus configured to acquire at least one facial image of said eye;
image-processing means configured to process said at least one facial image to determine a measured value of an outer diameter ($D_I$) of an iris of said eye; and
calculation means configured to determine a first value of said eye rotation center (P1) by mathematically calculating a distance ($d_{ERC}$) between a center of the sclera and an apex of the cornea as a function of said value of the outer diameter ($D_I$) of the iris of said eye and of a geometric model of an eye whereby the eye is modeled with one sphere (C1) for the sclera of the eye and one substantially spherical surface (C2) for the cornea of the eye, the position of the eye rotation center of the eye corresponding to a center (P1) of the sclera and being determined by the distance ($d_{ERC}$) between said center and an apex of the cornea and being determined based on a set of personal parameters ($L_E$, $d_{AC}$, $D_I$, $A_{GE}$, K) including at least the outer diameter ($D_I$) of the iris of the eye, each personal parameter ($L_E$, $d_{AC}$, $D_I$, $A_{GE}$, K) being distinct from said position ($d_{ERC}$) of the eye rotation center of the eye.

14. The method according to claim 1, wherein said first geometric dimension ($D_I$) of said eye comprises at least one of the following:
an outer diameter ($D_I$) of an iris of said eye;
a front and/or rear shape of a lens of said eye; and/or
a distance ($d_{AC}$) between a corneal apex and said lens of the eye or a pupil or a plane of the pupil of said eye.

15. The method according to claim 2, wherein said first geometric dimension ($D_I$) of said eye comprises at least one of the following:
an outer diameter ($D_I$) of an iris of said eye;
a front and/or rear shape of a lens of said eye; and/or
a distance ($d_{AC}$) between a corneal apex and said lens of the eye or a pupil or a plane of the pupil of said eye.

16. The method according to claim 3, wherein said first geometric dimension ($D_I$) of said eye comprises at least one of the following:
an outer diameter ($D_I$) of an iris of said eye;
a front and/or rear shape of a lens of said eye; and/or
a distance ($d_{AC}$) between a corneal apex and said lens of the eye or a pupil or a plane of the pupil of said eye.

17. The method according to claim 4, wherein said first geometric dimension ($D_I$) of said eye comprises at least one of the following:
an outer diameter ($D_I$) of an iris of said eye;
a front and/or rear shape of a lens of said eye; and/or
a distance ($d_{AC}$) between a corneal apex and said lens of the eye or a pupil or a plane of the pupil of said eye.

18. The method according to claim 1, wherein said geometric model is a model of the sclera and of the cornea of the eye, said sclera being modeled by a first sphere ($C_1$) having a first radius ($R_1$) and said cornea being modeled by a second sphere ($C_2$) having a second radius ($R_2$), said first sphere ($C_1$) and said second sphere ($C_2$) having a first center ($P_1$) and a second center ($P_2$) respectively, said first center ($P_1$) and said second center ($P_2$) defining an optical axis of said eye.

19. The method according to claim 2, wherein said geometric model is a model of the sclera and of the cornea of the eye, said sclera being modeled by a first sphere ($C_1$) having a first radius ($R_1$) and said cornea being modeled by a second sphere ($C_2$) having a second radius ($R_2$), said first sphere ($C_1$) and said second sphere ($C_2$) having a first center ($P_1$) and a second center ($P_2$) respectively, said first center ($P_1$) and said second center ($P_2$) defining an optical axis of said eye.

* * * * *